(12) United States Patent
Kieser et al.

(10) Patent No.: US 10,993,816 B2
(45) Date of Patent: May 4, 2021

(54) IN VIVO ROTATABLE PLIF ADDITIVELY MANUFACTURED AND READING SYSTEM THEREFOR

(71) Applicants: Brian Kieser, San Antonio, TX (US); Zeshan Hyder, Munster, IN (US); Thomas Zink, San Antonio, TX (US)

(72) Inventors: Brian Kieser, San Antonio, TX (US); Zeshan Hyder, Munster, IN (US); Thomas Zink, San Antonio, TX (US)

(*) Notice: Subject to any disclaimer, the term of this patent is extended or adjusted under 35 U.S.C. 154(b) by 196 days.

(21) Appl. No.: 16/412,558

(22) Filed: May 15, 2019

(65) Prior Publication Data

US 2019/0350673 A1 Nov. 21, 2019

Related U.S. Application Data

(60) Provisional application No. 62/673,198, filed on May 18, 2018.

(51) Int. Cl.
| | |
|---|---|
| *A61F 2/46* | (2006.01) |
| *A61F 2/44* | (2006.01) |
| *A61B 90/90* | (2016.01) |
| *A61F 2/30* | (2006.01) |
| *A61B 90/00* | (2016.01) |

(52) U.S. Cl.
CPC .......... *A61F 2/4611* (2013.01); *A61B 90/90* (2016.02); *A61F 2/447* (2013.01); *A61B 2090/397* (2016.02); *A61B 2090/3925* (2016.02); *A61B 2090/3937* (2016.02); *A61B 2090/3954* (2016.02); *A61B 2090/3966* (2016.02); *A61F 2002/3008* (2013.01); *A61F 2002/3071* (2013.01); *A61F 2002/30261* (2013.01); *A61F 2002/30331* (2013.01); *A61F 2002/30593* (2013.01); *A61F 2002/30622* (2013.01); *A61F 2002/30784* (2013.01); *A61F 2002/30828* (2013.01); *A61F 2002/30985* (2013.01)

(58) Field of Classification Search
CPC ......... A61B 90/90; A61F 2/447; A61F 2/4611
See application file for complete search history.

(56) References Cited

U.S. PATENT DOCUMENTS

| | | | |
|---|---|---|---|
| 2007/0282441 A1* | 12/2007 | Stream | A61F 2/30771 623/17.11 |
| 2010/0137988 A1* | 6/2010 | Markworth | A61F 2/447 623/17.16 |
| 2010/0152853 A1* | 6/2010 | Kirschman | A61F 2/447 623/17.11 |

(Continued)

*Primary Examiner* — Christian A Sevilla
(74) *Attorney, Agent, or Firm* — Brennan, Manna & Diamond, LLC

(57) ABSTRACT

A posterior lumbar interbody fusion (PLIF) implant that comprises a body with substantially parallel posterior and anterior sidewalls, and a pair of superior and inferior faces. The implant is inserted via an insertion tool within a depression in the sidewalls of the implant. The insertion tool is secured to the side walls of the implant to prevent any bending or breaking of the implant or the inserter during implantation. Once inserted, the implant may be rotated approximately 90 degrees within the disc space. Because of the shape and size of the implant, the effective height of the implant within a patient's disc space is increased upon rotation.

19 Claims, 7 Drawing Sheets

(56) References Cited

U.S. PATENT DOCUMENTS

| | | | |
|---|---|---|---|
| 2010/0168798 A1* | 7/2010 | Clineff | A61F 2/4611 |
| | | | 606/279 |
| 2010/0179594 A1* | 7/2010 | Theofilos | A61F 2/447 |
| | | | 606/247 |
| 2011/0230970 A1* | 9/2011 | Lynn | A61F 2/4611 |
| | | | 623/17.16 |
| 2011/0245923 A1* | 10/2011 | Cobb | A61F 2/442 |
| | | | 623/17.16 |

* cited by examiner

IN VIVO ROTATABLE PLIF ADDITIVELY MANUFACTURED AND READING SYSTEM THEREFOR

CROSS-REFERENCE TO RELATED APPLICATION

The present application claims priority from U.S. Provisional Patent Application Ser. No. 62/673,198 filed on May 18, 2018, which is incorporated herein by reference in its entirety.

FIELD OF THE INVENTION

The present invention relates to a vertebral implant, and more particularly to an additively manufactured posterior lumbar interbody fusion (PLIF) implant that can be rotated about its longitudinal axis once in the disc space to increase the amount of distraction. The present invention also relates to a carrier and reading system therefor, and methods of identifying and encoding implants, and systems for identifying and encoding implanted devices.

BACKGROUND OF THE INVENTION

A number of medical conditions can cause severe back pain including, without limitation, compression of spinal cord nerve roots, degenerative disc disease, tumors, and trauma. Intervertebral fusion is one surgical method of alleviating back pain. In an intervertebral fusion procedure, two adjacent vertebral bodies are fused together by removing the affected intervertebral disc and inserting posteriorly an implant that would allow for bone to grow between the two vertebral bodies to bridge the gap (oftentimes referred to as the disc space) created by the disc removal.

A number of different implant materials and implant designs have been used for intervertebral/interbody fusion and for vertebral body replacement with varying degrees of success. Current implant materials used include metals, radiolucent materials including plastics, elastic and polymeric materials, ceramic, and allografts. Current implant designs vary from threaded cylindrical implants to generally rectangular cages with teeth-like protrusions.

Additionally, for patients that require fusion surgery to treat such ailments as degenerative disc disease, deformity and instability, the PLIF cage has been shown to be somewhat effective. However, there remain a number of limitations associated with the use of the PLIF impaction design. For example, the force needed to hammer in such an implant can damage the patient's vertebral bodies. Additionally, most PLIF devices are inserted sideways with a manual tool that grips the exterior surface of the PLIF device, and then rotates the same within the disc space. However, because of the relatively weak sidewalls of existing PLIF devices, and the positioning of the manual tool on the exterior surface of the sidewalls of the PLIF device, the PLIF devices tend to either break or become deformed during the insertion procedure, or are incapable of exerting enough force on the adjacent vertebrae to achieve successful insertion of the PLIF device and/or the desired amount of distraction.

Therefore, there is a long felt need in the art for a rotatable PLIF implant that can be inserted into the disc space with less force and less trauma to the patient's vertebral bodies, and without bending, breaking or otherwise causing damage to the PLIF implant and/or the insertion tool. There is also a long felt need in the art for a rotatable PLIF implant that promotes bone growth and that is capable of including structurally encoded data that can be read after implantation via a plurality of non-invasive means. Finally, there is a long felt need in the art for an improved PLIF implant that is relatively easy to manufacture and use.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The present invention includes a PLIF implant comprising a body with substantially parallel posterior and anterior sidewalls, and a pair of superior and inferior faces. The implant also comprises at least one depression or opening in the anterior or posterior sidewalls for engagement by an insertion tool, and at least one chamfer on the superior and inferior faces to allow for easier insertion. The superior and inferior faces also comprise a rounded edge along a perimeter of the faces. The chamfer on the superior and inferior faces facilitates insertion of the implant in an oblique approach, so that a single implant provides balanced support to the spinal column.

In one embodiment of the present invention, the superior and inferior faces also comprise a plurality of undulating surfaces for contacting upper and lower vertebral endplates. Further, the implant may be manufactured with webbing or other honey-combed like structure or mesh on the lateral sections of the sidewalls to promote bone growth (or osteointegration) within the implant after implantation.

In another embodiment of the present invention, the implant is inserted via an insertion tool within the depression or slots that exist between the sidewalls of the implant and the keyhole support. The insertion tool comprises an elongated shaft defining a longitudinal axis and having a proximal end and a distal end. The proximal end comprises a handle and the distal end comprises a spaced apart grip member. The spaced apart grip member comprises bifurcated shaft portions which retain the implant there between during the implantation procedure.

Specifically, the bifurcated shaft portions of the insertion tool are inserted into the slots formed between the sidewalls of the implant and the keyhole support, and, at the same time, a key portion of the insertion tool is inserted into a slotted opening in the keyhole support, which secures the implant to the insertion tool and reduces the likelihood that the implant or insertion tool will bend or break during the implantation procedure. Once the implant has been inserted longitudinally into the disc space, the implant is rotated approximately 90 degrees within the disc space, and can be rotated in the clockwise or counter-clockwise direction. Because the implant is typically taller than it is wide, rotating the implant after implantation in the disc space can increase the amount of distraction or space between the adjacent vertebras. Nonetheless, the implant can also be positioned in a straight PLIF configuration as well (i.e., not rotated after implantation), depending on the wants and needs of the surgeon performing the procedure and/or the particular patient requirements.

In another embodiment of the present invention, the implant may be manufactured using additive manufacturing (AM) techniques. And, if not manufactured by AM techniques, the implant and inserter may be manufactured from titanium, specifically Ti 6 Al 4 V-ELI, or any other suitable material used for installation of the implant in a sterile environment or surgical setting.

Further, in one embodiment of the present invention, the PLIF implant may comprise a plurality of notches (or other radiopaque inclusions that interrupt an otherwise uniform surface) on the vertical rods of the sidewalls of the implant that can be coded to match the encoded markers that may be pressed into the device. Such structural encoding may be accomplished for instance through the use of eclipsing patterns of marks or notches in other planes within the PLIF implant (including subsurface planes), to reveal a pattern upon elucidation through reading illumination or through illumination-aided visual inspection or optical inspection, as described herein.

The displayed pattern may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices and a user interface comprising means for displaying information associated with the indicia based on the plurality of records. The encoded pattern may in turn be related to a unique numerical identifier corresponding to the associated manufacturer, serial number, installation data, patient, surgeon, or any surgical procedure information or other information that may be located in an external healthcare facility or other database.

The reading illumination may be that of any appropriate imaging modality such as those selected from the group consisting of visible light, UV light, x-ray, fluoroscopy, computed tomography, electromagnetic radiation, ultrasound, magnetic resonance imaging, positron emission tomography and neutron imaging, depending upon the nature and thickness of the implant body and the constituent adjacent first and second encoded regions and constituent series of shaped inclusions.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE FIGURES

While the specification concludes with claims particularly pointing out and distinctly claiming the present invention, it is believed that the present invention will be better understood from the following description in conjunction with the accompanying Figures, in which like reference numerals identify like elements, and wherein:

DETAILED DESCRIPTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
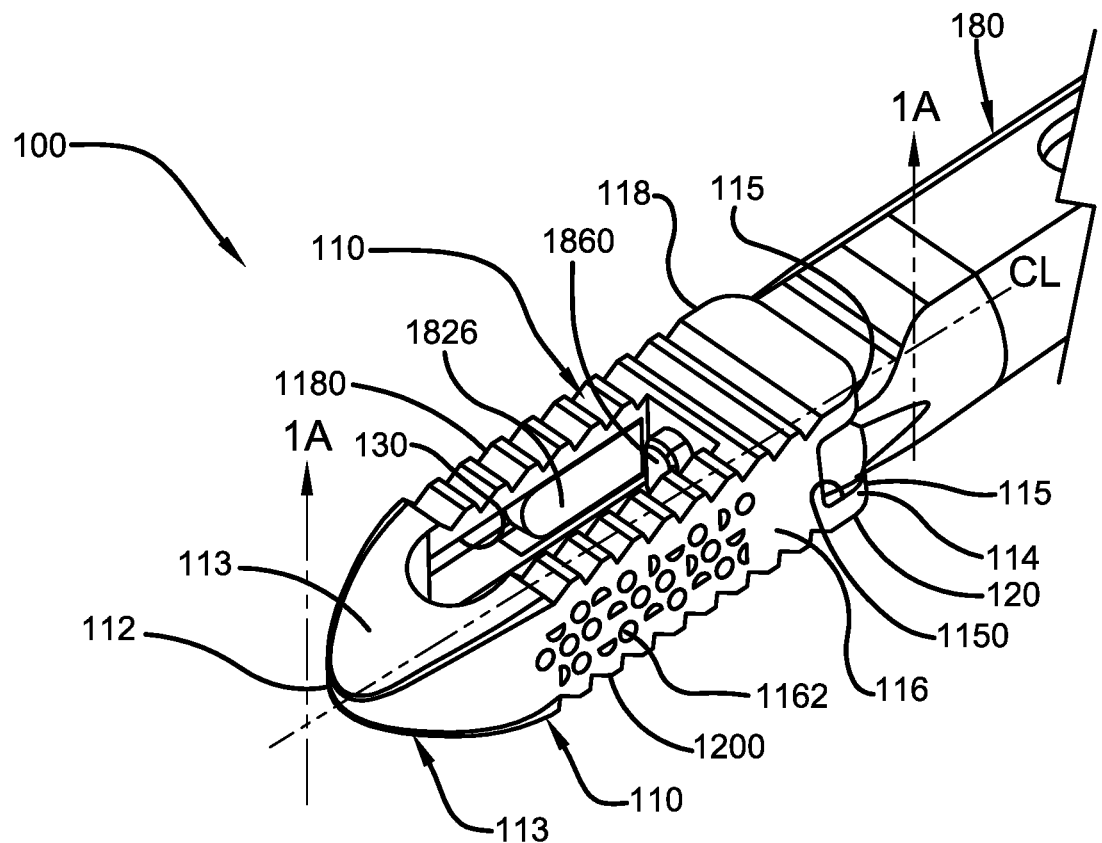
FIG. 1 is a perspective view of a PLIF implant removably attached to an inserter and in accordance with an embodiment of the present invention.

FIG. 1 is a perspective view of a posterior lumbar interbody fusion (PLIF) implant 100 in accordance with an embodiment of the present invention, attached to an insertion tool 180. The PLIF implant 100 is preferably comprised of a body portion 110 having a longitudinal center line axis CL extending from the front to the rear, a window 130 for promoting bone growth as explained more fully below, and a keyhole support 150 having an opening 152 formed therein for receipt of a portion of insertion tool 180, as described more fully below.

Figure 1A:
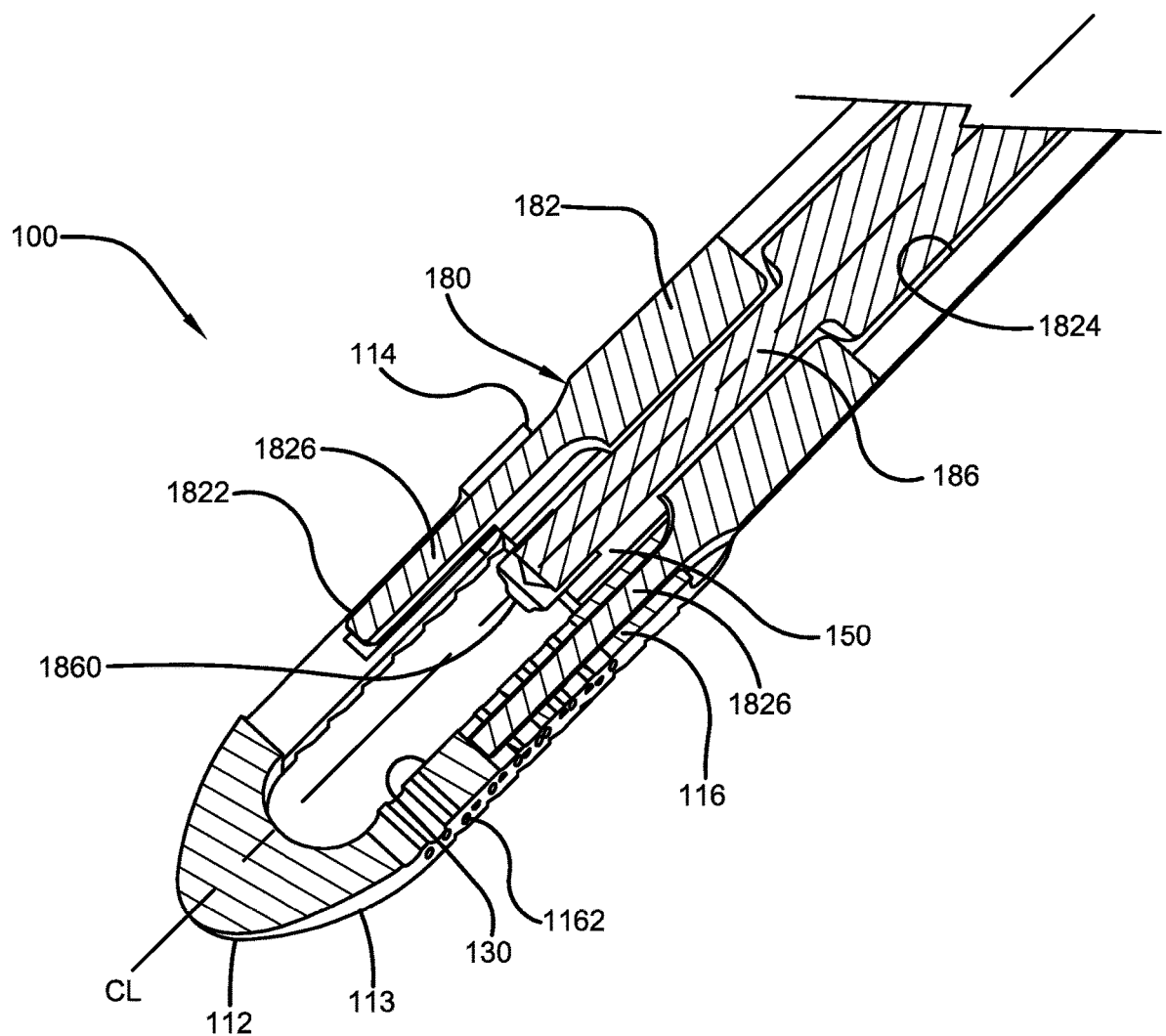
FIG. 1A is a cross-sectional view of the PLIF implant and inserter of FIG. 1 at cut line 1A-1A, and in accordance with an embodiment of the present invention.

Body portion 110 is preferably comprised of a superior or front end 112, a rear end 114, opposing sides 116, a top 118 and an opposing bottom 120. As best shown in FIGS. 1 and 1A, front end 112 is generally curved in shape and is comprised of one or more chamfered surfaces 113, preferably tapering off of the top 118 and bottom 120 in the direction of the front end 112. The chamfers 113 on front end 112 facilitate insertion of implant 100 in a generally oblique approach so that a single implant 100 provides the patient with balanced support to the spinal column once implanted.

As best shown in FIGS. 1 and 2-4, rear end 114 is comprised of two, generally parallel and spaced apart protrusions 115 with a valley or opening 1150 and keyhole support 150 positioned there between, the purpose of which will be explained more fully below. Ideally, the edges of rear end 114 will also be generally rounded or chamfered to facilitate easier implantation of implant 100 in a patient (not shown), but the same are not required to be.

Figure 2:
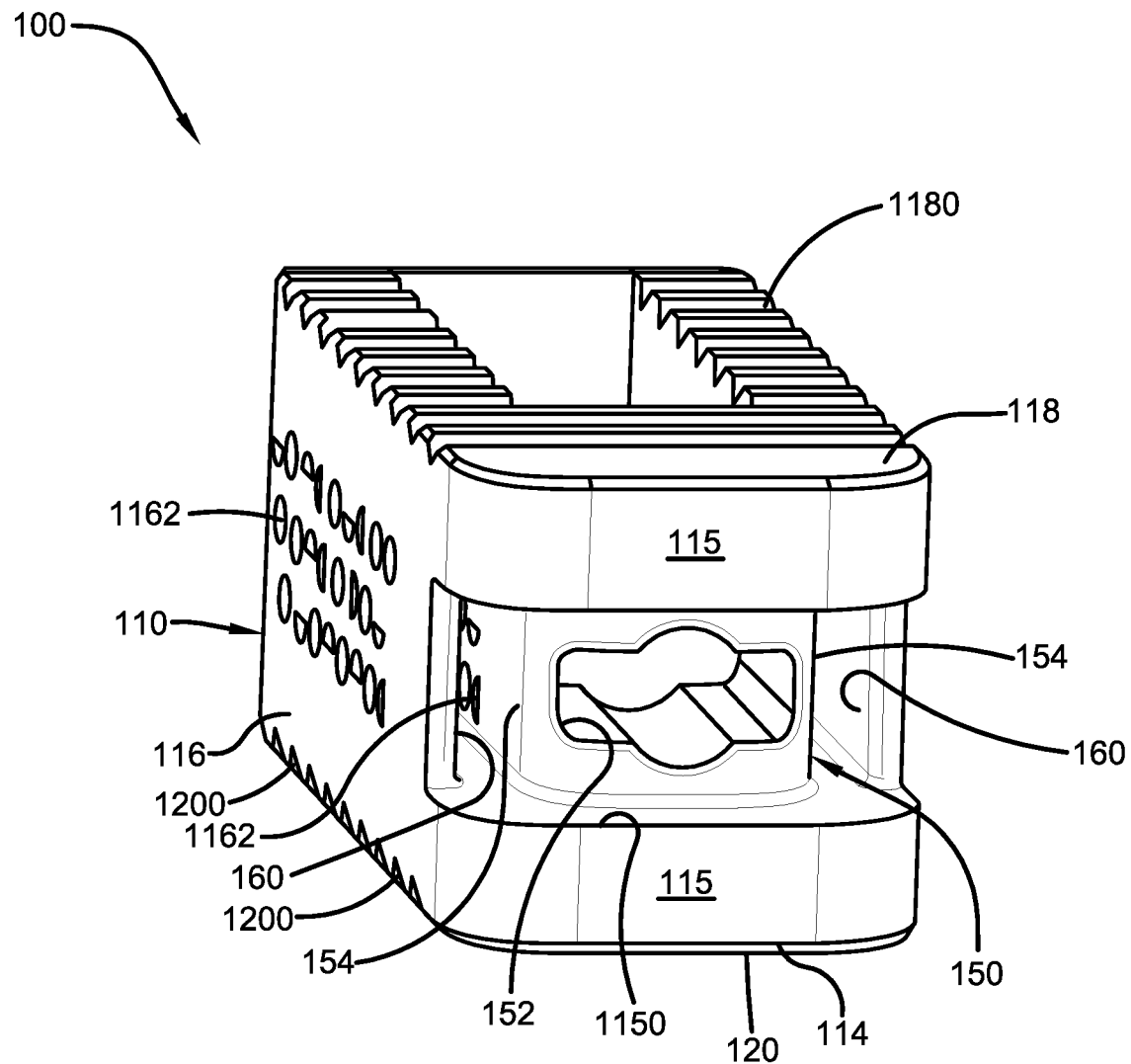
FIG. 2 is a back perspective view of a PLIF implant in accordance with an embodiment of the present invention.
Figure 3:
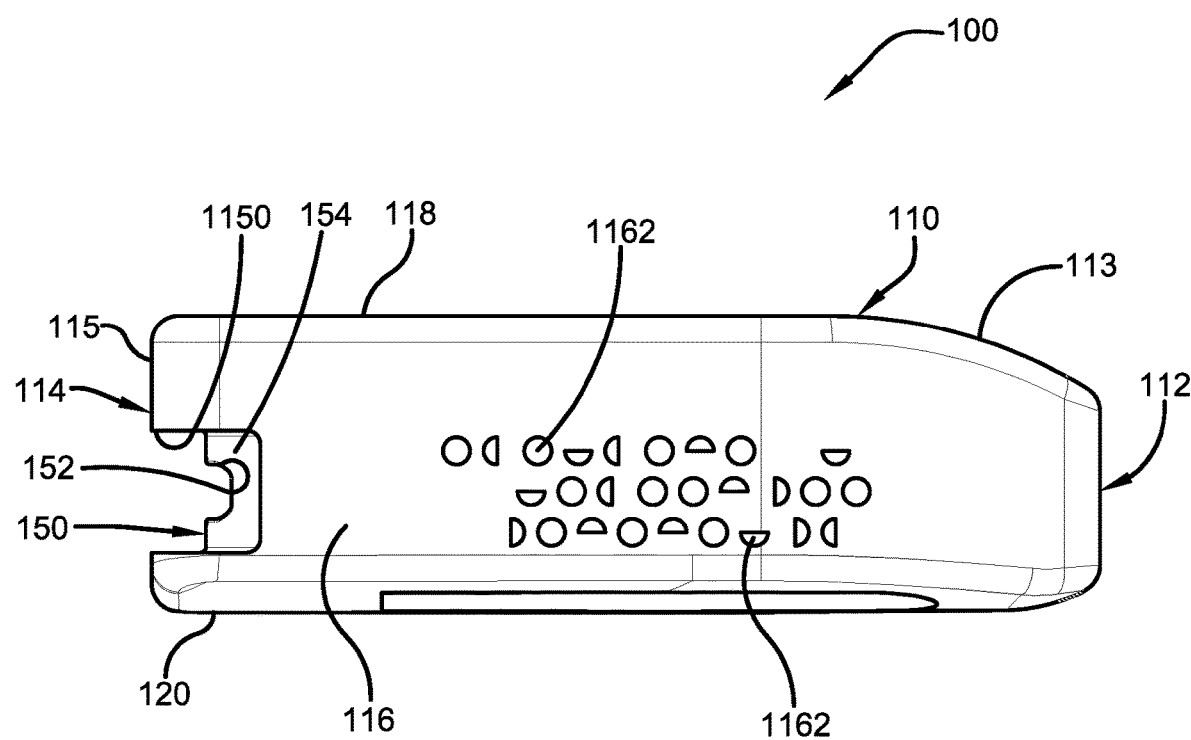
FIG. 3 is a side perspective view of a PLIF implant in accordance with an embodiment of the present invention.
Figure 4:
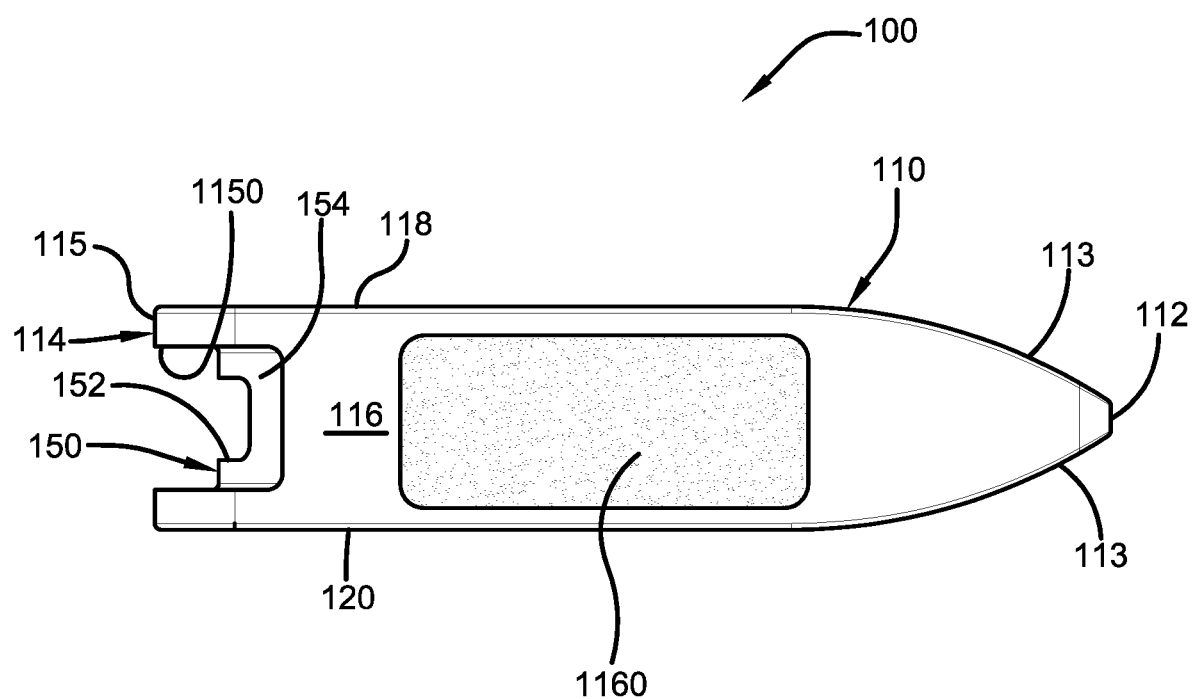
FIG. 4 is a side perspective view of an alternative PLIF implant having a mesh portion in accordance with an embodiment of the present invention.

As best shown in FIGS. 1-4, opposing sides 116 are generally parallel and spaced apart from one another, with window 130 and keyhole support 150 positioned there between. One or more of opposing sides 116 may further comprise webbing, mesh or other honey-comb like structure 1160 to promote bone growth within implant 100. More specifically, the webbed portion/honey-comb like structure 1160 of opposing side walls 116 of implant 100, an example of which is shown in FIG. 4, promotes osteo-integration and bone growth.

Further, as best shown in FIG. 3, one or more of sidewalls 116 of implant 100 may also comprise notches 1162 or other radiopaque inclusions that interrupt an otherwise uniform surface on sidewall 116 and that can be coded to match the encoded markers that may be pressed into the device. Such encoding may be accomplished for instance through the use of eclipsing patterns of marks or notches in other planes within the implant 100, to reveal a pattern upon elucidation through reading illumination or through illumination-aided visual inspection, optical inspection or any other non-invasive method, as described more fully herein.

The displayed pattern of notches 1162 may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices and a user interface comprising means for displaying information associated with the indicia based on the plurality of records. The encoded pattern may in turn be related to a unique numerical identifier corresponding to, by way of example and not limitation, the associated manufacturer, serial number, installation data, patient, surgeon, or surgical procedure information that may be located in an external healthcare facility or other database.

A typical embodiment of the structurally encoded implants 100 of the present invention may contain data that is not readily apparent to a viewer of the device structure. Further, encoding of the typical embodiments of the present invention is handled by physical means other than those accomplished through circuitry, electromagnetic or other, within the implant device itself or through a type of internal storage means such as magnetic storage means or the like. Such structurally encoded devices, as disclosed herein and described in relation to the typical and/or preferred embodiments of the present invention allow simplified production, maintenance, and/or operation costs for identification, storage, and/or retrieval of unique implant data while retaining a substantial amount of information with reduced probability for error.

Each of top 118 and bottom 120 may further comprise a plurality of undulating surfaces 1180 and 1200, respectively, for contacting upper and lower vertebral endplates upon successful insertion of implant 100 within the disc space. Undulating surfaces 1180 and 1200 are preferably comprised of a plurality of alternating ridges and valleys that help implant 100 to grip the vertebral implants and reduce the likelihood of implant 100 repositioning itself relative to the adjacent vertebral implants once properly installed, though it is contemplated that other structures could also be used for the same purpose without affecting the overall concept of the present invention.

As best shown in FIGS. 1-2, window 130 is preferably a generally rectangular continuous opening in body portion 110 that extends from top 118 to bottom 120, and is positioned between opposing sides 116. Window 130 promotes osteo-integration in the disc space, and through implant device 100. Although the shape and dimensions of window (i.e., length, width, and height) are important design parameters for good performance, window 130 may be any shape or size that ensures optimal performance during use or that satisfies surgeon and/or patient need or preference.

As best shown in FIG. 2, keyhole support 150 is preferably positioned towards the rear 114 of body portion 110 between protrusions 115 and is generally centered in valley or opening 1150. More specifically, keyhole support 150 is comprised of a slotted opening 152 therein and sidewalls 154 as illustrated in FIG. 2. Importantly, an opening or slot 160 is formed on each side of keyhole support 150 between keyhole support sidewalls 154 and opposing sides 116 for receipt of a portion of implant tool 180, as described more fully below. Sidewalls 154 may further comprise webbing, mesh or other honey-comb like structure 1160 thereon to promote osteo-integration, or notches 1162 as an alternative means of structurally encoding implant device 100, as discussed supra.

Although the dimensions (i.e., length, width, and height) and the exact shape of body portion 110 and its various components are important design parameters for good performance, body portion 110 may be any shape or size that ensures optimal performance during use or that satisfies surgeon and/or patient need or preference. Notwithstanding, the overall height of implant 100, measured from the top 118 to the bottom 120, will typically be greater that its width, as measured between opposing sides 116, so that when implant 100 is inserted sideways in between two vertebral implants (not shown) and rotated approximately 90 degrees (clockwise or counter-clockwise) about centerline CL, implant 100 will become "taller" in the disc space and apply force against the adjacent vertebral implants, thereby causing greater distraction, which is desirable.

Typically, the PLIF implant 100 of the present invention may be manufactured using additive manufacturing (AM) techniques, or using a combination of other molding or machining techniques (injection molding, machining, etc.) to produce the subject encoded implants. These additional techniques include, without limitation, material extrusion, vat photo polymerization, powder bed fusion, material jetting, binder jetting, sheet lamination and directed energy deposition. Typically, implant 100 is manufactured from titanium, specifically Ti 6 Al 4 V-ELI, but can be manufactured from any other suitable material as is known in the art for similar applications.

Figure 5:
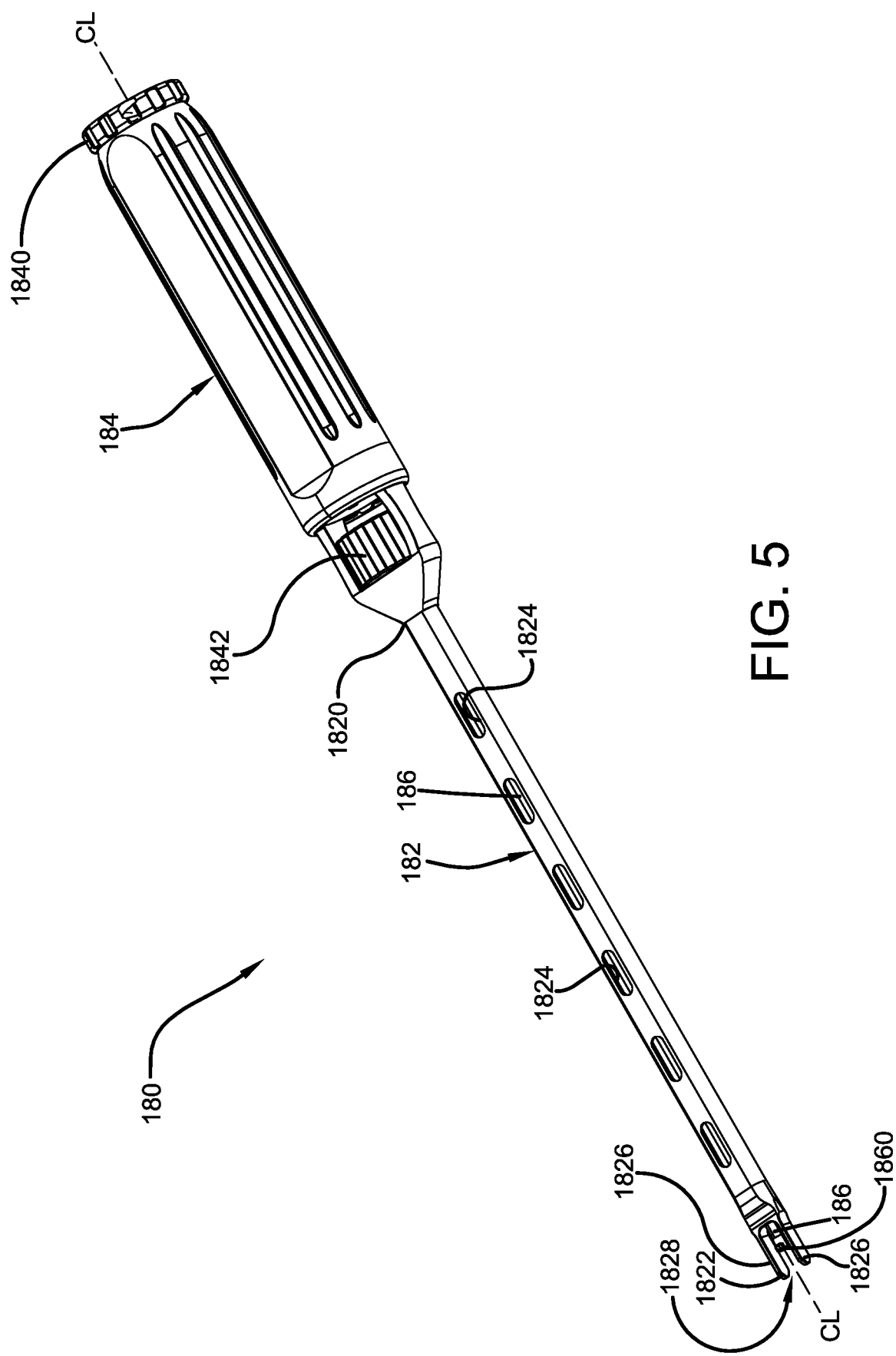
FIG. 5 is a perspective view of a PLIF implant inserter in accordance with an embodiment of the present invention.
Figure 6:
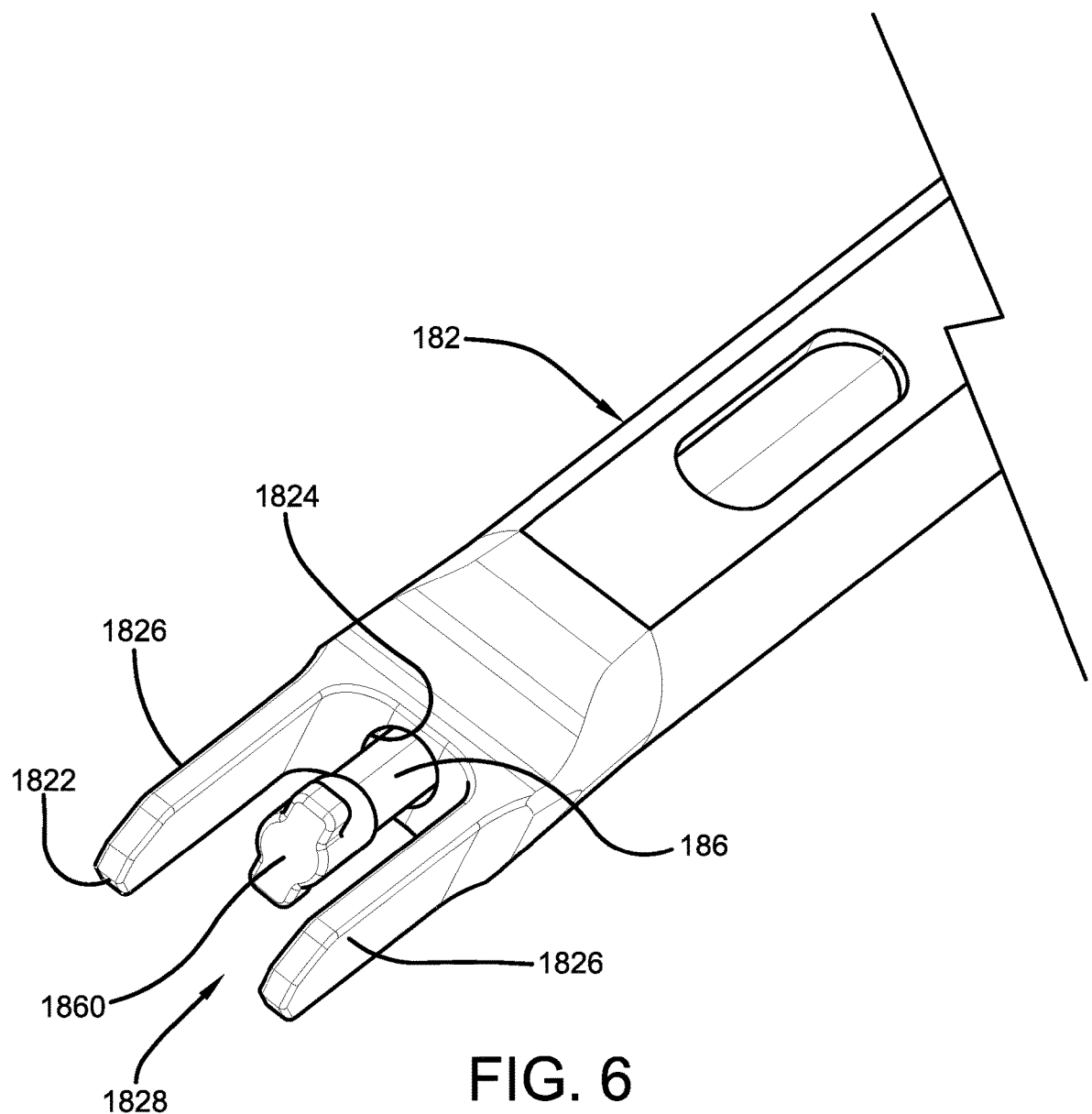
FIG. 6 is a perspective view of the distal end of the PLIF implant inserter of FIG. 5 and in accordance with an embodiment of the present invention.

As best shown in FIGS. 5 and 6, insertion tool 180 preferably comprises an elongated shaft 182, a handle 184 and a rotatable rod 186. More specifically, shaft 182 is comprised of a proximal end 1820 and a distal end 1822, and a longitudinal opening 1824 therein extending from said proximal end 1820 to said distal end 1822 for receipt of rod 186.

Handle 184 is located at the proximal end 1820 of shaft 182 and is preferably comprised of a solid metal, such as stainless steel, though other materials may also be used provided that said materials are suitable for use in a sterile environment or surgical setting. Handle 184 may have a scalloped gripping surface comprised of Radel® plastic or other suitable material to ensure steady handling of insertion tool 180, though any other durable handle known in the art could also be used. Handle 184 further comprises an impactor cap 1840 to aid in striking the handle 184 during insertion of implant device 100, as explained more fully below, and a thumb wheel 1842 mechanically attached to rod 186 so that rotation of thumb wheel 1842 will, in turn, also cause rod 186 to rotate within shaft 182 about centerline CL.

The distal end of elongated shaft 182 (i.e., opposite handle 184 and thumb wheel 1842) is formed into a spaced apart grip member, comprising bifurcated and spaced apart shaft portions 1826, as best shown in FIGS. 5 and 6. Shaft portions 1826 form a gap 1828 there between to securely retain the implant 100 during the implantation procedure. More specifically, shaft portions 1826 may be inserted into slot 160 between opposing sides 116 and keyhole support sidewalls 154, as explained more fully below.

Rod 186 is positioned within opening 1824 in elongated shaft 182 and extends from its mechanical connection with thumb wheel 1842 in the direction of the distal end 1822 of shaft 182 and into gap 1829. Rod 186 further comprises a key 1860 at its distal end for insertion into keyhole opening 152 in keyhole support 150, as more fully described below.

Having generally described a preferred embodiment of the implant device 100 and insertion tool 180 of the present invention, their function will now be generally described. A surgeon (not shown) desiring to install PLIF implant device 100 into a disc space (not shown) of a patient would attach implant 100 to insertion tool 180 by using the thumb wheel 1842 to rotate rod 186 so that key 1860 is inserted into opening 152 and shaft portions 1826 are inserted into the slots 160 between opposing sides 116 and keyhole support sidewalls 154. Because shaft portions 1826 are internal to body portion 110, and positioned between and supported by both opposing sides 116 and sidewalls 154, implant 100 and insertion tool 180 are less prone to failure, bending or other damage than prior art PLIF implants and insertion tools, which typically grip the PLIF implant on its exterior surface thereby causing damage thereto during the implantation procedure.

Once implant 100 is properly installed on insertion tool 180, the surgeon may insert implant 100 into a disc space in a patient between two vertebras. Importantly, chamfered surfaces 113 on front end 112 facilitate insertion of implant 100 in an oblique approach so that a single implant 100 provides a patient with balanced support to the spinal column. Once implant 100 has been inserted sideways in between two vertebral implants (not shown), implant 100 is rotated approximately 90 degrees (clockwise or counter-clockwise) about centerline CL and, because implant 100 is generally taller (as measured from top 118 to bottom 120) than it is wide (as measured between opposing sides 116), implant 100 will become "taller" upon rotation and apply force against the adjacent vertebral implants, thereby causing greater distraction, which is desirable. Further, once rotated, undulating surface 1180 on the top surface 118 of implant 100 and undulating surface 1200 on the bottom surface 120 of implant 100 will grip the adjacent surface of the vertebra and prevent unwanted slippage or repositioning of device 100 once installed in a patient's disc space.

Additionally, as explained more fully above, the presence of window 130 and mesh 1160 on one or more of opposing sides 116 and/or sidewalls 154 help to promotes osteointegration in the disc space, and through implant device 100. Similarly, the presence of notches 1162 in opposing sides 116, sidewalls 154 or any other location on implant 100 may permit implant 100 to be structurally encoded with a wide range of data including, without limitation, data pertaining to implant 100, the implant manufacturer, the patient, etc. Further, said structurally encoded information can be subsequently read and interpreted through a wide variety of non-invasive means including, without limitation, visible light, UV light and/or any medical imaging modality, such as at least one of x-ray, fluoroscopy, computed tomography, electromagnetic radiation, ultrasound, and magnetic resonance imaging.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A posterior lumbar interbody fusion (PLIF) implant comprising:
    a body portion having opposing sides, wherein the sides each comprise an exterior surface and a longitudinally extending interior surface;
    a window;
    a keyhole support with an opening therein; and
    a pair of slots formed between said opposing sides and the keyhole support.

2. The implant according to claim 1, wherein the body portion comprises at least one undulating surface and at least one chamfered surface.

3. The implant according to claim 1, wherein the implant is manufactured using additive manufacturing techniques.

4. The implant according to claim 1, wherein the implant is comprised of titanium.

5. The implant according to claim 1, wherein the body portion comprises at least one surface having webbing thereon.

6. The implant according to claim 1, wherein the implant further comprises a plurality of structural markings that represent data.

7. The implant according to claim 6, wherein said data is read via a system selected from the group consisting of visible light, UV light, x-ray, fluoroscopy, computed tomography, electromagnetic radiation, ultrasound, visible light, UV light, x-ray, fluoroscopy, computed tomography, electromagnetic radiation, ultrasound, magnetic resonance imaging, positron emission tomography and neutron imaging.

8. A posterior lumbar interbody fusion (PLIF) implant for insertion into a disc cavity comprising:
    a body portion with substantially parallel posterior and anterior sidewalls, wherein the sidewalk each comprise an exterior surface and a longitudinally extending interior surface and a pair of superior and inferior faces having at least one chamfer; and
    a keyhole support, wherein said keyhole support and the posterior sidewall forms a first slot and said keyhole support, and the anterior sidewall forms a second slot.

9. The implant according to claim 8, wherein a height of body portion, as measured between the superior and inferior faces, is greater than a width of body portion, as measured between posterior and anterior sidewalls.

10. The implant according to claim 8, wherein the implant further comprises a window and at least one mesh surface.

11. The implant according to claim 8, wherein the body portion further comprises at least one undulating surface.

12. The implant according to claim 8 wherein the implant is manufactured using additive manufacturing techniques.

13. The implant according to claim 8, wherein the implant further comprises a plurality of structural markings that represent data.

14. The structurally encoded system according of claim 13, wherein the data is read via a system selected from the group consisting of visible light, UV light, x-ray, fluoroscopy, computed tomography, electromagnetic radiation, ultrasound, visible light, UV light, x-ray, fluoroscopy, computed tomography, electromagnetic radiation, ultrasound, magnetic resonance imaging, positron emission tomography and neutron imaging.

15. A structurally encoded implant system comprising:
- an implant having a body portion, a window and a keyhole support with an opening therein; and
- an insertion tool comprised of a key portion positioned between two spaced apart shaft portions;
- wherein a first slot and a second slot are formed between the keyhole support and longitudinally extending interior surfaces of opposing sides of the implant for receipt of said two spaced apart shaft portions; and
- wherein the implant is configured for interbody fusion.

16. The structurally encoded implant system of claim 15, wherein the body portion is further comprised of at least one chamfered surface, at least one undulating surface, and at least one mesh surface.

17. The structurally encoded system according of claim 15, wherein said body portion further comprises a plurality of markings that represent a structurally encoded data.

18. The structurally encoded system according of claim 17, wherein the structurally encoded data is read via a system selected from the group consisting of visible light, UV light, x-ray, fluoroscopy, computed tomography, electromagnetic radiation, ultrasound, visible light, UV light, x-ray, fluoroscopy, computed tomography, electromagnetic radiation, ultrasound, magnetic resonance imaging, positron emission tomography and neutron imaging.

19. The structurally encoded implant according to claim 17, wherein the structurally encoded data is related to a unique numerical identifier corresponding to an associated manufacturer, serial number, installation data, patient, surgeon, or surgical procedure information.

\* \* \* \* \*